United States Patent
Aguilar Rubido et al.

(10) Patent No.: US 6,358,933 B1
(45) Date of Patent: Mar. 19, 2002

(54) FORMULATION OF NUCLEIC ACID AND ACEMANNAN

(75) Inventors: Julio Cesar Aguilar Rubido; Verena Lucila Muzio Gonzalez; Gerardo Enrique Guillen Nieto; Eduardo Penton Arias; Maria de Jesus Leal Angulo; Dagmara Pichardo Diaz; Enrique Iglesias Perez; Antonieta Herrera Buch; Belquis Sandez Oquendo; Alexis Musacchio Lasa, all of Habana; Diogenes Quitana Vazquez, Pinar del Rio; Lissere Crombet Menedez, Habana, all of (CU)

(73) Assignee: Centro de Ingenieria Genetica Y Biotechologia, Habana (CU)

( * ) Notice: Subject to any disclaimer, the term of this patent is extended or adjusted under 35 U.S.C. 154(b) by 0 days.

(21) Appl. No.: 09/530,925
(22) PCT Filed: Sep. 3, 1999
(86) PCT No.: PCT/CU99/00004
§ 371 Date: May 5, 2000
§ 102(e) Date: May 5, 2000
(87) PCT Pub. No.: WO99/13704
PCT Pub. Date: Mar. 16, 2000

(30) Foreign Application Priority Data

Sep. 7, 1998 (CU) .................................. 126/98

(51) Int. Cl.$^7$ ........................ A61K 31/70; A61K 31/715
(52) U.S. Cl. .......................................... 514/44; 514/54
(58) Field of Search ........................................... 514/44

(56) References Cited

PUBLICATIONS

Chinnah et al: Vaccine Jul. 1992; 10:551–7.*
Sugimoto et al: FEBS Let Arp. 1995; 363:53–56.*
Toda et al. Immunol Sep. 1997; 92:111–17.*

* cited by examiner

Primary Examiner—Robert A. Schwartzman
Assistant Examiner—Q Janice Li
(74) Attorney, Agent, or Firm—Hoffmann & Baron, LLP

(57) ABSTRACT

The present invention is for a formulation comprising a nucleic acid vaccine and an immunoenhancing amount of acemannan, whereby the acemannan enhances immune response, in a host, to the vaccine. The present invention is also for a method of enhancing the immune response of a host to a nucleic acid vaccine by administering a formulation comprising a nucleic acid vaccine and acemannan.

12 Claims, 4 Drawing Sheets

First Schedule

| | | |
|---|---|---|
| Group 1-100µg ADN/ PBS 1X | | IM |
| Group 2-100µg ADN/ PBS 1X | | IP |
| Group 3-100µg ADN/ OxCa (0.5mg/mL) | | IP |
| Group 4-100µg ADN/ OxCa (0.5mg/mL)+acemannan (3mg/mL) | | IP |
| Group 5-100µg ADN/ acemannan (3mg/mL) | | IP |

First Schedule

| | |
|---|---|
| Group 1-100μg ADN/ PBS 1X | IM |
| Group 2-100μg ADN/ PBS 1X | IP |
| Group 3-100μg ADN/ OxCa (0.5mg/mL) | IP |
| Group 4-100μg ADN/ OxCa (0.5mg/mL)+acemannan (3mg/mL) | IP |
| Group 5-100μg ADN/ acemannan (3mg/mL) | IP |

Second Schedule

Group 1-100μg ADN/ PBS 1X                                      IM

Group 2-100μg ADN/ acemannan (3mg/mL)                IM

Third Schedule:

| | |
|---|---|
| Group 1-100µg pEACM7 (parental)/PBS | IM |
| Group 2-100µg pEACM7CR2/PBS | IM |
| Group 3-100µg pEACM7CR2/Acemannan 3mg/mL | IM |
| Group 4-100µg pEACM7CR2/PBS | IP |
| Group 5-100µg pEACM7CR2/Acemannan 3mg/mL | IP |

Fourth Schedule

Group 1- 100µg DNA/ PBS 1X    IM
Group 2- 200µg Opc/ PBS 1X    IN
Group 3- 100µg ADN/ 200µg Opc    IN
Group 4- 100µg ADN/ 200µg Opc +acemannan (3mg/mL)    IN
Group 5- Positive control
Group 6- Negative control
Group 7- mAb 279, 5C
Group 8- mAb 154, D-11

FORMULATION OF NUCLEIC ACID AND ACEMANNAN

BACKGROUND OF THE INVENTION

The present invention is related to the field of medicine, particularly to the development of new immunoenhancing formulations allowing an increase of the amount and quality of the immune response to vaccine antigens.

The technical aim of the proposed invention is the development of formulations that are capable of increasing the levels of the immune response to the nucleic acid-based vaccine.

The successful use of adjuvants to enhance this new kind of vaccines is not obvious. Recently, new compounds capable of enhancing the nucleic acid-based vaccines have been found. Inclusive, one of the first findings in the field of DNA immunization was the impossibility of alum to enhance this kind of vaccine, and this is the most generally used adjuvant in vaccines in the market.

The use of the direct immunization with DNA began in 1990. Nowadays the research is developed in the field of preventive vaccines as well as in the genetic therapies of somatic cells to treat cancers, infections and metabolic diseases. DNA vaccines have some advantages compared to the other vaccine strategies. As the attenuated or recombinant viruses, the plasmidic vectors activates T-CD8+ cytotoxic cells (Wang, B. et al. 1993 Proc. Natl. Acad. Sci. U.S.A. 90, 4156–4160), (Xiang, Z. Q. et al. 1994 Virology 199, 132–140).

Once inoculated, DNA is capable of continually expressing their constitutive genes for months (Wolff, J. A. et al. 1990 Science 247: 1465) and it doesn't seem to be pathologic or mutagenic to the target cell, because the majority of plasmids exist in a circular and non-replicative and non-integrative form (Wolff, J. A. et al. 1990 Science 247: 1465).

There's no induction of anti DNA antibodies (Xiang, Z. Q., et al. 1995 Virology 209: 569) neither serious inflammatory reactions or other complications in the site of the inoculation. Furthermore, the plasmidic DNA can be easily manipulated and it is relatively cheap in big quantities with high levels of purity (Tsuji, T. et al. 1997 Eur. J. Immunol. 27: 782–787).

Although the mechanisms involved in the induction and the maintenance of the immune response are not clear yet, the strategy of coinoculation of plasmids coding for cytokines and costimulatory factors has been successfully used. It is known that there are some other factors involved in the response, i.e. the own characteristics of the vector which could affect the rate of transcription (Davis et al. 1993 Hum. Gene ther., 4, 151–159).

Nowadays it is known that myocytes are able to present antigens associated to the Major Histocompatability System (MHC) Class I (Pardoll, D. M. and Beckerrieg, A. M. 1995 Immunity 3: 165)(Cohen, J. 1993 Science. 259: 1745), but these cells express MHC class I and II molecules poorly. For an efficient antigenic presentation, a costimulatory signal or antigen-independent second signal for the activation and proliferation of T cells after the antigen-specific interaction of the T cell receptor (TCR) and the MHC is essential (Bluestone, J. A., 1995 Immunity 2: 555).

With the use of plasmids coding for the costimulatory molecules B7-1 and B7-2, an increased co-stimulatory signal can be expressed in the myocytes (Hohlfeld, R. y Engel, A. G., 1994 Immunol Today, 15, 269) inducing higher levels of proliferation and activation of specific T cells for the introduced antigen. Applied to the tumor immunology, it has been probed that the poor immunogenicity of some tumors is due to the lack of costimulatory molecules. The transduction of DNA coding for B7-1 or B7-2 molecules in tumor cells greatly enhanced the antitumoral immunity (Townsend, S. E. y Allison, J. P. 1993 Science, 259: 368) Gajewski, T. F.,1996 J. Immunol. 156: 465)(Yang, G., et al. 1995 J. Immunol. 154: 2794).

Recently it has been reported that the inoculation in the same adenovirus of genes coding for the hepatitis B surface antigen (HBsAg) and the B7-1 molecule induced a higher cytotoxic response specific for the HBsAg compared with the gene of the viral antigen alone (He, X. S. et al. 1996 Proc. Natl. Acad. Sci., U.S.A. 93: 7274). It has also been demonstrated that the co-inoculation of plasmidic DNA coding for B7–1 with the vaccinal DNA of HIV-1 increased the specific cellular response for HIV-1 compared to the inoculation of HIV-1 plasmidic DNA alone. It could be demonstrated that the increase in cellular immunity with B7–2 depended on γIFN. (Tsuji, T. et al. 1997 Eur. J. Immunol. 27: 782–787). In this article, any enhancing effect related to the coinoculation of B7-1 couldn't be demonstrated. This phenomena can be explained taking into consideration that the B7-2 are more rapidly induced by the antigen presenting cells (APC) than the B7-1 molecules (Hathcock, K. S. et al. 1994 J. Exp. Med. 180: 631) that's why B7-2 are preferred for the initial antigenic presentation. Similar results have been obtained by other authors, demonstrating the enhanced response of CD8+ cytotoxic lymphocytes (Kim, J. J. et al. 1997 Nature Biotechnology 15: 641–646). The γ-IFN is a pleiotropic cytokine capable of enhancing T-cell mediated responses, upregulating the expression of the MHC determinants. The treatment of myoblasts in culture with γ-IFN increased the susceptibility to cytolysis by T cells and also provided signals for T cell lines proliferation. However, it has been found that the coinoculation of a plasmid coding for the G protein of Rabia Virus and the plasmid coding for γ-IFN did not increase the antiviral immune response (Xiang, Z. et al. 1995 Immunity 2, 129–135).

Recent studies have shown that the effect of the γ-IFN depends on the promotor used (Xiang, Z. et al. 1997 Vaccine Vol. 15(8) 896–898). The colony Stimulating Factor of Granulocytes and Macrophages (GMCSF) has also been coinoculated as a plasmid (Xiang, Z. et al. 1995 Immunity 2, 129–135). Primary immune responses can be induced with this cytokine (Tao, M. H. et al. 1994 Nature 362, 755–758) by activation or recruiting of professional antigen presenting cells (Heufler, C. et al 1988 J. Exp. Med. 167, 700–705).

In 1995, Xiang and cols evidenced that the enhancing effect of the plasmid coding for GM-CSF over the humoral immune response against the G protein of Rabbia Virus after the co-inoculation of the two plasmids. Both plasmids coinoculated separately in the time (hours) did not generate any effect in the antibody response to the Rabbia Virus. It suggests that cotransfection of individual APC cells or the proximity of the APC to the secreting cell are important factors, showing the local activity of the cytokine (Xiang, Z. et al. 1995 Immunity 2, 129–135).

The increase of the antibody response observed by coinoculation with the plasmid expressing GM-CSF shows that the primary effect of GM-CSF over the Th cell response, resulting in an increase in the activation of specific antigen B cells. In experiments using cytokine depending cell lines, the lack of response to IL4 indicates that DNA vaccines induce principally Th cells, as previously shown and that the cytokine GM-CSF enhance this pattern of response (Xiang, Z. et al 1995 Immunity 2, 129–135).

IL-12 is a very important immunomodulatory cytokine. It has been demonstrated that the expression plasmid coinoculated along with a plasmid coding for HIV-1 protein, enhanced the HIV-1 specific cell mediated immunity. Although the mechanisms involved in the induction and maintaining of the immune response are not clear, this kind of strategy could be successful (Takashi, T. et al. 1997 J. Immunol. 158: 4008–4013).

In addition to their adjuvant properties, the treatment of HIV-1 positive patients with IL-12 retarded the progression to AIDS. (Clerici, M. et al. 1993 Science 262: 1721). It also normalizes some parameters, for example, the cytotoxic activity mediated by natural killer cells (NK) (Chehimi, J. et al. 1992 J. Exp. Med. 175: 789). IL-12 also inhibits apoptosis of CD4+ cells (Randrizzani, M. et al. Cell Immunol. 161: 14).

In coadministration studies of plasmids coding for IL-6 and haemaglutinin inoculated using the Accell gene gun, mice were protected to challenge with influenza virus. Mice receiving the plasmid expressing haemaglutinin only exhibited an accelerated clearance of the viral challenge but they were not protected against the infection. Mice coinoculated did not show the virus in lung after the challenge. (Larsen, D. L., et al. 1998 J. Virol. 72(2) 1704–1708).

The design of efficient gene delivery systems has been important for gene therapy. Recently the association and stability of plasmid DNA coding for ovalbumin and polymeric particles with a size of micrometers has been studied: biodegradable microspheres of lactic and coglicolic acid, poli-DTHcarbonate (a pseudopoliaminoacid) and poliestiren particles of almost 1 μm. All of them has different size and electric charge and has been assayed in mucosal and parental immunizations. Higher responses can be obtained after the administration of DNA associated to particles compared to the inoculation of free DNA. The intranasal (i.n.) inoculation in particulated systems generates high responses in sera (Alpar, H. O. et al. 1997 Biochemical Society Transactions 25, 337S).

The adjuvant effect of Ubenimex (UBX), an anticancer immunomodulator, over an anti-HIV-1 vaccine based in DNA was evaluated in a murine model. The UBX was coinoculated intramuscularly in balb/c mice generating IgG antibody response higher 103 and 105 times than those obtained without UBX. This compound also generated a higher delayed targeted hypersensitivity DTH), as well as cytotoxic responses (CTL), specific against HIV. The pattern of cytokines of restimulated lymphocytes showed that the UBX increased the IL-2 and γ-IFN levels and decreased the production of IL-4. The analysis of immunoglobin subclasses showed an increase in the IgG2 a levels in the group adjuvated with UBX as well as a decrease in the synthesis of IgG1 and IgE. The clinic use of UBX as an adjuvant for DNA vaccines is attractive due to their low immunogenicity and toxicity (Sasaki, S. et al. 1998 Clinical and Experimental Immunology 111-1: 30–35).

The use of mannans covering chemical structures as the N-t-butyl N' tetradecyclamino-propionamidina (diC14 amidina), enhanced the antigen specific immune response to a plasmid coding for a gene of the gpl6 O protein of HIV-1. The covering of diC14 with the mannan significantly increased the antigen-specific DTH response induced by the DNA. The CTL activity was also enhanced with this mixture. The immunomodulatory effect was inhibited when mice were treated using antibodies against γ-IFN in vivo, evidencing that γ-IFN plays an important role in the induction of cellular immunity generated by DNA vaccines. Subclasses analysis and cytokine pattern showed that DNA vaccines incorporated in mannan covered particles of diC14 amidine generated a Th 1 response (Sasaki, S. et al. 1997 Eur J Immunol 27 (12): 3121–3129).

The lipopolysaccharide derivative monophophoril lipid A has been evaluated with DNA vaccines through i.n. and i.m. routes with a plasmid coding for HIV-1 antigen. Both routes generated similar levels of cellular immunity but the IgA secreted in the gut was higher in the case of animals inoculated intranasally. The MPL-A enhanced the immune response through both routes (Sasaki, S. et al. 1998 Infection and Immunity 66(2): 823–826).

An important factor related to the type of response induced is the cellular compartment in which the antigen coded by the plasmidic vector is expressed. In a study with the forms secreted, anchored to membrane or intracellular of the D protein of Bovine Herpesvirus-1, capable of inducing neutralizing titers consistently, a difference in rate of seroconversion could be evidenced. Mice immunized with the authentic form -membrane anchored-, as well as the correspondent to the secreted form, seroconverted before those immunized with the cytosolic form of the glycoprotein D. During the first 14 weeks, mice immunized with the authentic form, developed the higher IgG levels. Those immunized with the cytosolic form had the lowest geometric mean of antibody titers but in the week 23, titers increased over titers obtained by the authentic form. The pattern of cytokines of lymphocytes from spleen was characteristic of Th1 responses, with a production of γ-IFN for all the antigen forms. For the secreted form, the IgG isotype pattern in ELISA did not correlate with the cytokine pattern (Lewis P. J. et al. 1997 Vaccine 15 (8) 861–864).

The relation between cellular localization and effectivity was studied using ovalbumin as antigen model. The secreted form was, surprisingly, the one generating higher antibody titers and CTL responses. (Boyle J.S. et al. 1997 International Immunology 9, 12 1897–1906).

Recent works have evidenced that the quantity of the immune response depends on the immunization route. Higher antibody titers were obtained by intradermal immunization compared to the intramuscular route in mice inoculated with DNA as well as with proteins. Although DNA immunizations can achieve similar levels of IgG to those obtained with the soluble protein, the avidity of the antibodies against ovalbumin was 100 to 1000 times higher with the plasmid inoculated through the route intramuscular and intradermal respectively compared to the soluble protein control. The IgG subclasses analysis evidenced an increase in the IgG2 a response in the case of the plasmid inoculated i.m. along with an increase of the γ-IFN production. IgG1 was the predominant subclass in the case of i.d. inoculation of soluble proteins and DNA, with a detectable production of IL-4. The CTL response was obtained only after the immunization with DNA. The DNA immunization differs from the immunization using proteins due to their capacity to generate strong CTL responses and the higher avidity of the generated antibodies, both parameters are very important in the design of vaccines. (Boyle J. S. et al. 1997 PNAS 94 (26): 14626–14631).

Many complex carbohydrates of natural origin stimulate the cells of the immune system and the reticulum-endothelial system (Davis, S. E. 1975 Am. Chem. Soc. Sympos. Series 15, Jeanes A. Hodge J. Eds. Am. Chem. Soc. Washington D.C.). Among these are the polymers of plants and funguses as the glucans, dextrans and lentinans, all of which are glucose polymers, and the mannans, among which are found the glucomannans and the galactomannans. Also found are the levans and xylans (Tizard, I. R. et al. 1989 Mol. Biother 1:290–296). The activity of many of these polyglycans on the macrophages (having glucan and mannan receptors) include the induction of phagocytosis and the secretion of cytokines, leucotriens and prostaglandines. The lentinan, a glucan that is common in mushrooms, stimulates the cell and antibody response in sheep erythrocytes while levan is mytogenic for B cells and a macrophage activator (Simon, P. M. 1994 Exp. Opin. Invest. Drugs 3 (3):223–239).

The acemannan is a mannan composed of mannose with 0 acetylations in approximately 8 out of every 10 remains. It is extracted as a major component of the mucilaginous substance or gel of the leaf of Aloe barbadensis Miller, medicinal plant used throughout history. Different tests in vitro indicate that mannans activate the monocytes and macrophages inducing the production of γ-IFN, factor-α of tumoral necrosis, GM-CSF, IL-1β and IL-6 (Peng, S. Y. et al. 1991 Mol. Biother. 3: 79–87). The acemannan potentiates the generation of cytotoxic T lymphocytes (CTL) (Womble, D. et al. 1988 Int. J. Immunopharmacol. 10:967–974), the cytotoxic activity of Natural Killer (NK) cells (Marshall G. D. et al. 1993, J. Immunol. (part II) 150: Abstr 1381), and also, slightly, the in vitro human alloresponse.

The increase of the cytotoxic activity and the secretion of γ-IFN supports the antiviral and antitumoral therapeutic use of acemannan. Its antiretroviral activity was evidenced in animals in the case of feline leukemia (Sheets, M. A. et al. 1991 Mol. Biother. 3: 41–45). Clinical assays in AIDS and cancer patients are currently in course.

A few patent applications have been solicited recently describing the use of acemannan as an adjuvant in vaccines. (McAnalley, B. H. EP 0 619 117 A2), (Nordgrem, R. M. WO 93/14195), (Aguilar, J. C. et al. CU27/ 1997) but the use of acemannan in vaccine formulations containing DNA as an antigen or any formulation with a nucleic acid in particular have never been covered.

One of the main problems of DNA-based vaccines is their poor generation of antibodies. The most common form to solve this problem is the introduction of necrosis inducing compounds in the muscles a few days before the innoculation of DNA in the regenerating muscle. The response after the introduction of the DNA in the normal muscle is not as good as in regenerating muscle, needing a practical development in this aspect to make a DNA vaccine a realistic strategy in front of the classical vaccination (Davis, H. L. et al. 1994 Vaccine 12 (16): 1503–1509).

SUMAMRY OF THE INVENTION

The present invention is related to the field of medicine, particularly to the use of new adjuvant formulations with vaccine antigens. The technical objective pursued with this invention is, precisely, the development of formulations that are able to increase and/or modulate the immune response of the organism to nucleic acid-based vaccines.

With this aim, a formulation was developed that contained as the main components the DNA and the acemannan in adequate proportions. The formulations of this invention are applicable in the pharmaceutical industry as vaccine formulations for human and veterinary use.

DETAILED DESCRIPTION OF THE INVENTION

In the present invention we report for the first time a vaccine formulation, having as its main components the acemannan polysaccharide and the nucleic acid vaccine in adequate proportions.

This formulation is a novelty due to the potentiation of the immune response generated after the mixing of both components.

These results support the introduction of acemannan-nucleic acid formulations with higher levels of-immunogenicity in vaccine formulations directed to the immunoprofylaxis and immunotherapeutic diseases caused preferentially by intracellular pathogens and cancer.

Nowadays, the mechanisms involved in the potential of acemannan are unknown. One proposed mechanism involves macrophagues and dendritic cells which has specific receptors specifics for antigenic patterns presented on the pathogen surfaces. Due to a chemoatractant characteristic, a strong monocytemia can be generated in the inoculation site.

Due to the viscous consistency of acemannan, it becomes an active vehicle which increases the antigen permanency in the inoculation site. We don't discard other activities such as the induction of cytokines, the activation of phagocytosis mechanisms and the recruiting of different cell populations of the immune system increasing the antigen presenting activity.

The formulation object of this invention can be immunized, according to the species, with a volume from 10 μL to 5 mL and a dose of 0.001 to 5 mg of nucleic acid. The acemannan dose varies from 0.001 mg/mL to 0.5 mg/mL of total hexose concentration, equivalent to a range of 0.01 to 5 mg/mL of lyophilized weight in the final vaccine formulation.

The low reactogenicity of acemannan regarding the new generation adjuvant along with the T independent response against the acemannan are very attractive characteristics of the kind of formulations.

EXAMPLES OF PERFORMANCE

Example 1

With the aim of evaluating the immune enhancing activity of acemannan on plasmids, to be used in DNA based vaccines, immunization schedules were carried out by the intraperitoneal route in male balb/c mice of 8 to 12-weeks of age. The plasmid used has the promoter of cytomegalovirus and codes for the protein β-galactosidase ((β-gal). The immunenhancing activity was quantified by immuno-assay (ELISA) to determine the IgG titers against β-gal in sera. Inoculations and extractions were performed on days 0, 15 and 30 and −2 (preimmune), 45, 90 and 120.

The results were processed using the student t test: $p<0.05$ was considered a significant difference.

Figure 1:
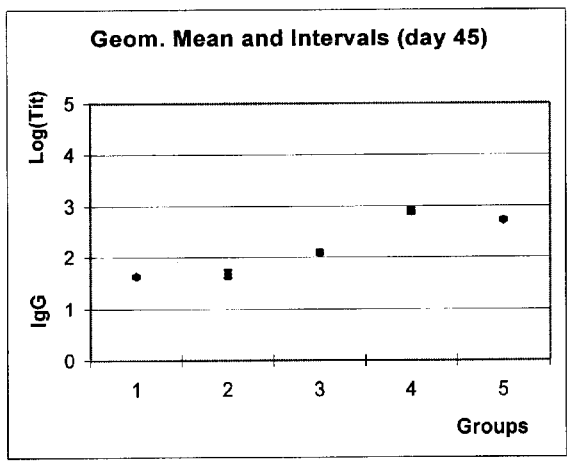
FIG. 1. Schedule of three doses (days 0, 15 and 30). Extraction on days 45, 90 and 120. All groups were inoculated with 100 μg of plasmid in a volume of 100 μL. The group 1 was inoculated intramuscularly, the other groups were immunized intraperitoneally.
Figure 1:
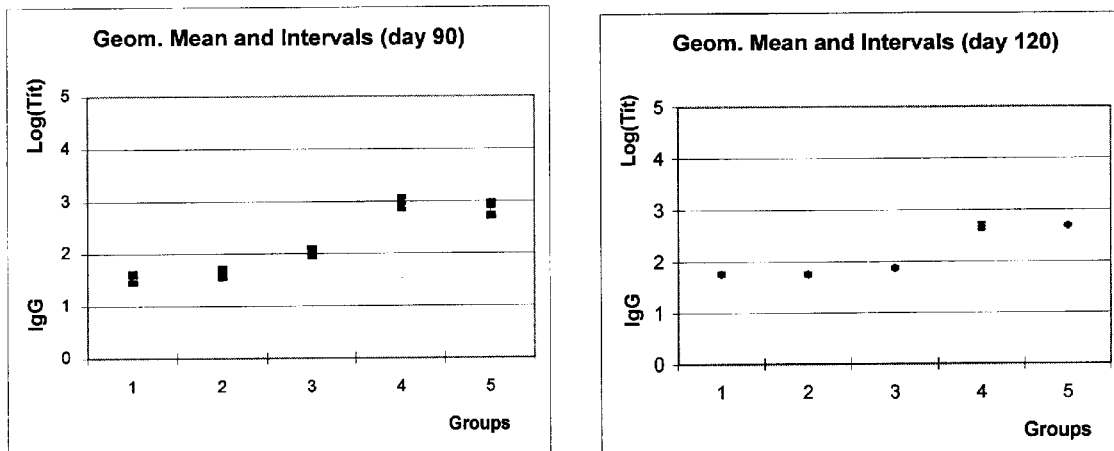

It was demonstrated that using acemannan along with pCMVβgal, enhanced antibody responses can be achieved, with significantly higher titers to the response obtained inoculating the plasmid in PBS. In general, the titers in the intraperitoneally inoculated groups (groups 4 and 5) were significantly higher to the titers obtained in groups 2 and 3. The difference generated on day 45 when calcium oxalate salts were added to a concentration of 0.5 mg/mL (group 4) was not maintained on days 90 and 120 (FIG. 1).

The inoculation of the plasmid was performed in absence of muscle necrosis or previous preparation of muscles. This could explain why the antibody titers are so poor after the inoculation of pCMV(βgal in PBS (group 1)).

Example 2

Figure 2:
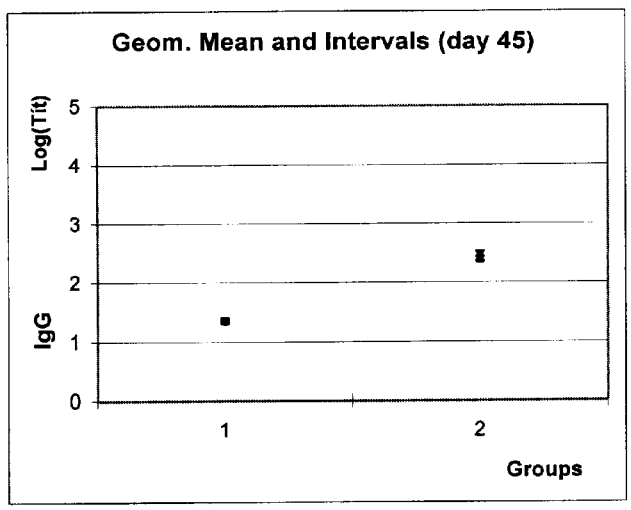
FIG. 2. Schedule of three doses (days 0, 15 and 30). Extraction was on day 45. Both groups were inoculated intramuscularly with 100 μg of plasmids in a volume of 100 μL.

With the aim of demonstrating the enhancing activity using the intramuscular route. A formulation was prepared mixing the polysaccharide acemannan and the pCMVβgal plasmid. This formulation was intramuscularly administrated to a group of 8 mice. As a control, the same quantity of plasmid was administrated in PBS (FIG. 2).

The statistical analysis of results was performed using the Student t test: $p<0.05$ was considered a significant difference.

It was demonstrated that acemannan can be formulated and used with pCMVβgal successfully. The group 1 (with acemannan) generated higher antibody titers compared to the same quantity of DNA administrated in PBS (group 2) when inoculated intramuscularly both preparations.

We neither used a previously prepared muscle or any necrosis producer to induce any kind of regeneration state in the immunized mice muscle.

Example 3

Figure 3:
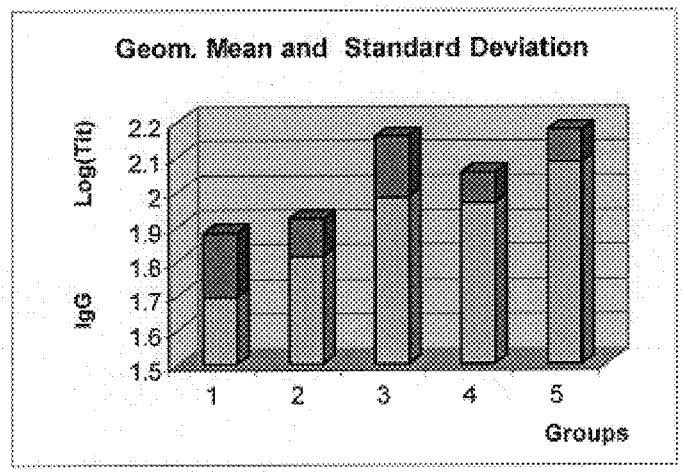
FIG. 3. Schedule of 5 doses (days 0, 21, 44, 64 and 76). Extraction was on day 92. All groups were innoculated using 100 μg of plasmids in a volume of 100 μL. The immunization routes were: intramuscular (i.m.) (groups 1–3) and intraperitoneal (i.p.)(groups 4 and 5).
Figure 4:
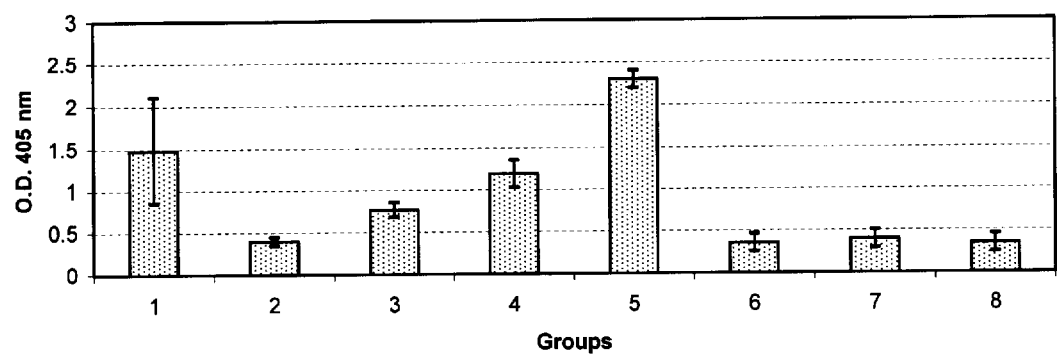
FIG. 4. Schedule of 4 doses (days 0, 14, 28, 42). Extraction was on day 56. Mice were inoculated intramuscularly and intranasally with 100 μg of plasmids in a volume of 100 μL and 50 μL respectively.
Figure 4:
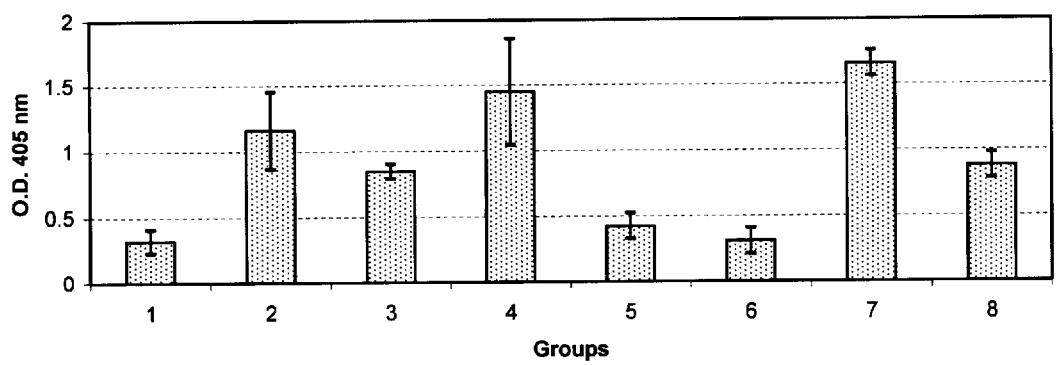

With the aim of demonstrating the immunoenhancing activity through the i.m. and i.p. routes, a formulation of acemannan and the plasmid pAEC-M7CR2 was prepared and administered to groups of 8 balb/c mice. The protein coded by this plasmid is a chimeric recombinant polypeptide bearing HIV-1 epitopes (CR2). As a control, the same quantity of plasmid in PBS was administered through both routes (FIG. 3), furthermore, the parental plasmid -a non coding plasmid was also tested and regarded as a placebo formulation.

The statistical analysis of results was performed using the Student t test: $p<0.05$ was considered a significant difference.

It was demonstrated, using the acemannan formulation (0.35 mg/mL of acem. +100 μg of plasmid per dose), for both routes, that it is possible to obtain anti-CR2 antibody responses significantly superior to the responses obtained by the plasmid innoculated in PBS (group 2).

We neither used a previously prepared muscle or any necrosis producer to induce any kind of regeneration state in the immunized mice muscle.

Example 4

With the aim of evaluating the immune enhancing activity of acemannan on plasmid DNA protein complexes inoculated through mucosal route, an immunization schedule was carried out by the intranasal route in female Balb/c mice of 6 to 8 weeks of age. An expression vector, containing the β-galactosidase reporter gene, under the control of human citomegalovirus promoter (pCMVβ-gal) was used. This plasmid was acomplexed with the Opc protein of *Neissena meningitidis*. The size of plasmid DNA-protein complexes was less than 5 μm. The immunoenhancing activity was quantified by immunoassay (ELISA) to determine serum IgG titers against β-galactosidase. Inoculations were performed on days 0, 14, 28 and 42 and serum samples were taken 15 days after the last inoculation (at day 56).

Results were processed using the student t test: $p<0.05$ was considered a significant difference.

It was demonstrated, that serum IgG antibody response against β-galactosidase, 15 days after the last inoculation, was higher when pCMVβ-gal plasmid DNA-Opc protein complexes were used along with acemannan, than when such complexes were inoculated alone.

We claim:

1. A formulation comprising a nucleic acid needing a protein and an immunoenhancing amount of acemannan, whereby the acemannan enhances humoral immune response, in a host, to said protein.

2. A formulation according to claim 1, wherein the nucleic acid is DNA.

3. A formulation according to claim 1, wherein the nucleic acid is RNA.

4. A method of enhancing humoral immune response, in a host, to protein encoded by a nucleic acid comprising administering to said host a formulation comprising a nucleic acid and an immunoenhancing amount of acemannan, whereby the acemannan enhances humoral immune response, in said host, to said protein.

5. A method according to claim 4, wherein the nucleic acid is DNA.

6. A method according to claim 4, wherein the nucleic acid is RNA.

7. An improvement to a nucleic acid vaccine formulation, wherein the improvement comprises combining a nucleic acid vaccine formulation with acemannan, whereby the acemannan increases humoral immune response, in a host, to said formulation.

8. An improvement according to claim 7, wherein said nucleic acid is DNA.

9. An improvement according to claim 7, wherein said nucleic acid is RNA.

10. In a method of generating humoral immune response, in a host, to a nucleic acid vaccine, an improvement to the method comprising combining said nucleic acid vaccine with acemannan, whereby the acemannan increases the humoral immune response, in said host, to said vaccine.

11. An improvement according to claim 10, wherein said nucleic acid is DNA.

12. An improvement according to claim 10, wherein said nucleic acid is RNA.

* * * * *

UNITED STATES PATENT AND TRADEMARK OFFICE
CERTIFICATE OF CORRECTION

PATENT NO. : 6,358,933 B1
DATED : March 19, 2002
INVENTOR(S) : Rubido et al.

It is certified that error appears in the above-identified patent and that said Letters Patent is hereby corrected as shown below:

Column 3,
Line 44, now reads "103 and 105 times" should read -- $10^3$ and $10^5$ times --;
Line 60, now reads "gp16 0 protein"; should read -- gp160 protein --;

Column 8,
Line 27, now reads "nucleic acid needing a protein"; should read -- nucleic acid encoding a protein --.

Signed and Sealed this

Sixteenth Day of July, 2002

Attest:

JAMES E. ROGAN
Attesting Officer     Director of the United States Patent and Trademark Office